(12) United States Patent
Takahashi et al.

(10) Patent No.: US 9,518,961 B2
(45) Date of Patent: Dec. 13, 2016

(54) LIQUID CHROMATOGRAPH AND COLUMN OVEN USED THEREFOR

(71) Applicant: SHIMADZU CORPORATION, Kyoto-shi, Kyoto (JP)

(72) Inventors: Kazuya Takahashi, Kyoto (JP); Yosuke Iwata, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 167 days.

(21) Appl. No.: 14/422,467

(22) PCT Filed: Jul. 23, 2013

(86) PCT No.: PCT/JP2013/069844
§ 371 (c)(1),
(2) Date: Feb. 19, 2015

(87) PCT Pub. No.: WO2014/030479
PCT Pub. Date: Feb. 27, 2014

(65) Prior Publication Data
US 2015/0192549 A1   Jul. 9, 2015

(30) Foreign Application Priority Data
Aug. 24, 2012   (JP) ................... 2012-185044

(51) Int. Cl.
*G01N 30/16* (2006.01)
*G01N 30/54* (2006.01)
(Continued)

(52) U.S. Cl.
CPC .............. *G01N 30/16* (2013.01); *G01N 30/30* (2013.01); *G01N 30/54* (2013.01); *G01N 2030/027* (2013.01)

(58) Field of Classification Search
None
See application file for complete search history.

(56) References Cited

U.S. PATENT DOCUMENTS

2002/0087937 A1   7/2002   Muth et al.
2008/0121015 A1   5/2008   Heuvel et al.

FOREIGN PATENT DOCUMENTS

JP   2002-267644 A   9/2002
JP   2008-129013 A   6/2008

OTHER PUBLICATIONS

International Search Report dated Oct. 29, 2013, issued in corresponding application No. PCT/JP2013/069844.
(Continued)

*Primary Examiner* — Michael A Lyons
*Assistant Examiner* — Jean Morello
(74) *Attorney, Agent, or Firm* — Westerman, Hattori, Daniels & Adrian, LLP (57) ABSTRACT

A difference between sensitivities among different solvents is preliminarily set as a device constant, using a calibration factor Ge, in a calibration-factor holding part. On the other hand, the sensitivities of gas sensors are measured for each gas sensor, but this measurement is not performed on all solvents and is performed on only a certain solvent, and a threshold value resulted therefrom is held as a reference threshold value $V_{tho}$ in a reference-threshold-value holding part. A threshold value $V_{th}$ for another solvent is determined from the reference threshold value $V_{tho}$ for the certain solvent and from the calibration factor Ge as the device constant according to $V_{th} = V_{tho} \times Ge$.

6 Claims, 8 Drawing Sheets

(51) Int. Cl.
*G01N 30/30* (2006.01)
*G01N 30/02* (2006.01)

(56) References Cited

OTHER PUBLICATIONS

Figaro, "Product information, gas sensor, flammable gas detection", Aug. 23, 2012, "http://www.figaro.co.jp/product/docs/tgs813_productinfo_rev01.pdf", cited in the Specification.

LIQUID CHROMATOGRAPH AND COLUMN OVEN USED THEREFOR

TECHNICAL FIELD

The present invention relates to a liquid chromatograph including a high-speed liquid chromatograph, and relates to a column oven used therefor.

BACKGROUND ART

In a liquid chromatograph, separation analysis is performed while a separation column is maintained at a constant temperature. The separation column is housed within a column oven in order to maintain the column at a constant temperature. The column oven is provided with a temperature control mechanism for maintaining the column oven at a constant temperature. As the temperature control mechanism, a block heater, for example, is provided as a heat source, and an air circulation system is employed in order to circulate the heat through the column.

As a mobile phase of a liquid chromatograph, a volatile solvent such as methanol, acetonitrile, or isopropyl alcohol (IPA) is used in some cases. Then, within the column oven, the separation column is connected to an analysis flow path through a joint, and, in some cases, the mobile phase leaks from this connection portion. When the mobile phase includes a volatile solvent, a vaporized gas is generated from the leaked mobile phase. When the vaporized gas is flammable, an explosive limit exists. Therefore, in order to prevent the vaporized gas concentration within the column oven from exceeding the explosive limit, a gas sensor is provided within the column oven, and the indication from the gas sensor is monitored such that the explosive limit is not exceeded.

The monitoring is performed by reading a voltage value output from the gas sensor to determine a leak sensor value from this voltage value and setting a leak threshold value with respect to the leak sensor value. Usually, the leak threshold value is set to be, for example, 1/10 or 1/20 of the explosive limit, in order to provide a margin. Then, when the leak sensor value exceeds the leak threshold value, an alert is issued, or the operation of the liquid chromatograph is stopped, in order to prevent the explosion.

On the other hand, an explosive limit concentration differs depending on the solvent. For example, ethanol has an explosive limit concentration of about 43000 ppm, while acetonitrile has an explosive limit concentration of about 30000 ppm. Therefore, differentiation of leak threshold values for a gas sensor depending on types of solvents has been already performed (refer to Patent Document 1). In a method in this Patent Document 1, each of the plural types of solvents is injected into a column oven so that its concentration reaches a concentration serving as a threshold value, a detected value from the gas sensor is individually measured for each solvent, and each detected value is set as a threshold value. Patent Document 1 is premised on a sensitivity characteristic that changes with a change in the gas sensor over time, and, in order to calibrate the sensitivity change over time, solvents are injected into each column oven, and the threshold value is directly measured for each solvent every calibration.

PRIOR ART DOCUMENTS

Patent Documents

Patent Document 1: JP-A No. 2002-267644

Non-Patent Documents

Non-Patent Document 1: FIGARO product information, gas sensor, flammable gas detection [online], [searched on Aug. 23, 2012], Internet (URL: http:/www.figaro.co.jp/product/docs/tgs813_productinfo_rev01.pdf)

SUMMARY OF THE INVENTION

Problems to be Solved by the Invention

In the method in Patent Document 1, since it is necessary to perform actual measurement by injecting each solvent into the oven every calibration, calibration manipulations are complicated.

Therefore, the present invention aims at simplifying manipulations for setting a threshold value by a gas sensor.

Solutions to the Problems

The present inventors have found that even when gas sensors have the same type, sensitivities of the gas sensors largely vary from one another (device differences) while gas sensors of the same type have a constant ratio between the sensitivities to vaporized gasses of different solvents.

The present invention is based on this founding and, thus, in the present invention, a difference between sensitivities to different solvents is preliminarily set as a device constant, using a calibration factor Ge. On the other hand, the sensitivities of gas sensors are measured for each gas sensor, but this measurement is not performed on all solvents and is performed on only a certain solvent, and a threshold value resulted therefrom is held as a reference threshold value. A threshold value for another solvent is determined from the reference threshold value for the certain solvent and from the calibration factor Ge as the device constant.

Namely, a column oven according to the present invention includes: a gas sensor that detects a vaporized gas of a solvent forming a mobile phase; a reference-threshold-value holding part that holds, as a reference threshold value $V_{tho}$, a threshold value determined from a detected value resulting from measurement by the gas sensor, for a vaporized gas of a certain solvent having a lower concentration than an explosive limit concentration; a calibration-factor holding part that preliminarily holds, as a device constant, a calibration factor Ge indicating a difference between sensitivities of the gas sensor to different solvents; a threshold-value calibration part that calculates a threshold value $V_{th}$ from the reference threshold value $V_{tho}$ held in the reference-threshold-value holding part and from the calibration factor Ge held in the calibration-factor holding part, according to $$V_{th} = V_{tho} \times Ge \qquad (1),$$

when a type of a solvent to be used is input; and a liquid leakage detection part that compares a detected value from the gas sensor with the threshold value calculated by the threshold-value calibration part to detect a liquid leakage within the column oven, during use of the column oven.

The sensitivity of the gas sensor has temperature dependency, and therefore, it is preferable to also take the temperature dependency into account when it is desired to determine the threshold value more accurately. Therefore, in a preferable aspect of the present invention, the column oven further includes a temperature-characteristic holding part that holds a temperature characteristic. Again, the temperature characteristic is not individually measured for each mounted gas sensor, but is preliminarily set as a device constant. Then, the threshold-value calibration part calculates the threshold value $V_{th}$, further based on the temperature characteristic held in the temperature-characteristic holding part.

The sensitivity of the gas sensor also has humidity dependency, and therefore, it is preferable to take the humidity dependency into account when it is desired to determine the threshold value more accurately. Therefore, in another preferable aspect of the present invention, the column oven further includes a humidity-characteristic holding part that holds a humidity characteristic. Again, the humidity characteristic is not individually measured for each mounted gas sensor, but is preliminarily set as a device constant. Then, the threshold-value calibration part calculates the threshold value $V_{th}$, further based on the humidity characteristic held in the temperature-characteristic holding part.

In a preferable aspect, the column oven may include only either one of the temperature-characteristic holding part and the humidity-characteristic holding part, so that the threshold-value calibration part calculates the threshold value $V_{th}$ based on the temperature characteristic or the humidity characteristic in the provided holding part, or may include both the temperature-characteristic holding part and the humidity-characteristic holding part, so that the threshold-value calibration part calculates the threshold value $V_{th}$ based on both the temperature characteristic and the humidity characteristic.

In a further preferable aspect, the column oven includes a low-ignition-point solvent type holding part that holds a type of a solvent having a lower ignition point. Then, when the type of the solvent to be used is input and when the input type of the solvent to be used agrees with the type of the solvent held in the low-ignition-point solvent type holding part, a display unit is caused to provide display for urging the user to be careful.

In a further preferable aspect, the reference-threshold-value holding part holds reference threshold values in plural stages, as the reference threshold value $V_{tho}$, and an alarm or another output form is differentiated depending on a liquid leakage detected based on a threshold value derived from among the reference threshold values in the plural stages. The threshold value for a certain solvent is for detecting a liquid leakage at a lower concentration than the explosive limit concentration of a vaporized gas of this solvent. Based on the reference threshold values in the plural stages, threshold values in plural stages are calculated for each solvent. Concentrations of a vaporized gas detected based on these threshold values have plural stages including concentrations closer to and farther from the explosive limit concentration. Therefore, when a liquid leakage is detected based on each of the threshold values in the stages, a different operation is performed according to each of the threshold values in the stages, so that in the event of a liquid leakage corresponding to a lower gas concentration farthest from the explosive limit concentration, only an alarm is displayed on the display device, and thereafter in the event of a liquid leakage corresponding to a gas concentration closer to the explosive limit concentration, an operation for stopping the operation of the liquid chromatograph is performed. This enables ensuring the safety of the column oven, without obstructing the operation of the liquid chromatograph.

The present invention is also directed to a liquid chromatograph such as a high-speed liquid chromatograph. A liquid chromatograph includes a liquid supply unit that supplies a mobile phase to an analysis flow path including a separation column, a sample injecting unit that injects a sample into the analysis flow path between the liquid supply unit and the separation column, and a detection unit that detects a sample ingredient eluted from the separation column. Then, in the present invention, the column oven according to the present invention is used as a column oven for performing temperature control on the separation column.

Effects of the Invention

In the present invention, a difference between sensitivities to different solvents is not measured for each solvent using a gas sensor mounted in a column oven, but is preliminarily set as a device constant (calibration factor Ge). Actual measurement by the mounted gas sensor is performed on only a certain solvent, and a threshold value resulting from this measurement is held as a reference threshold value. Then, since a threshold value for another solvent is determined from the reference threshold value for the certain solvent and from the calibration factor Ge as the device constant, calibration manipulations for determining a threshold value for a leak sensor value for each solvent become simplified.

EMBODIMENTS OF THE INVENTION

Figure 1:
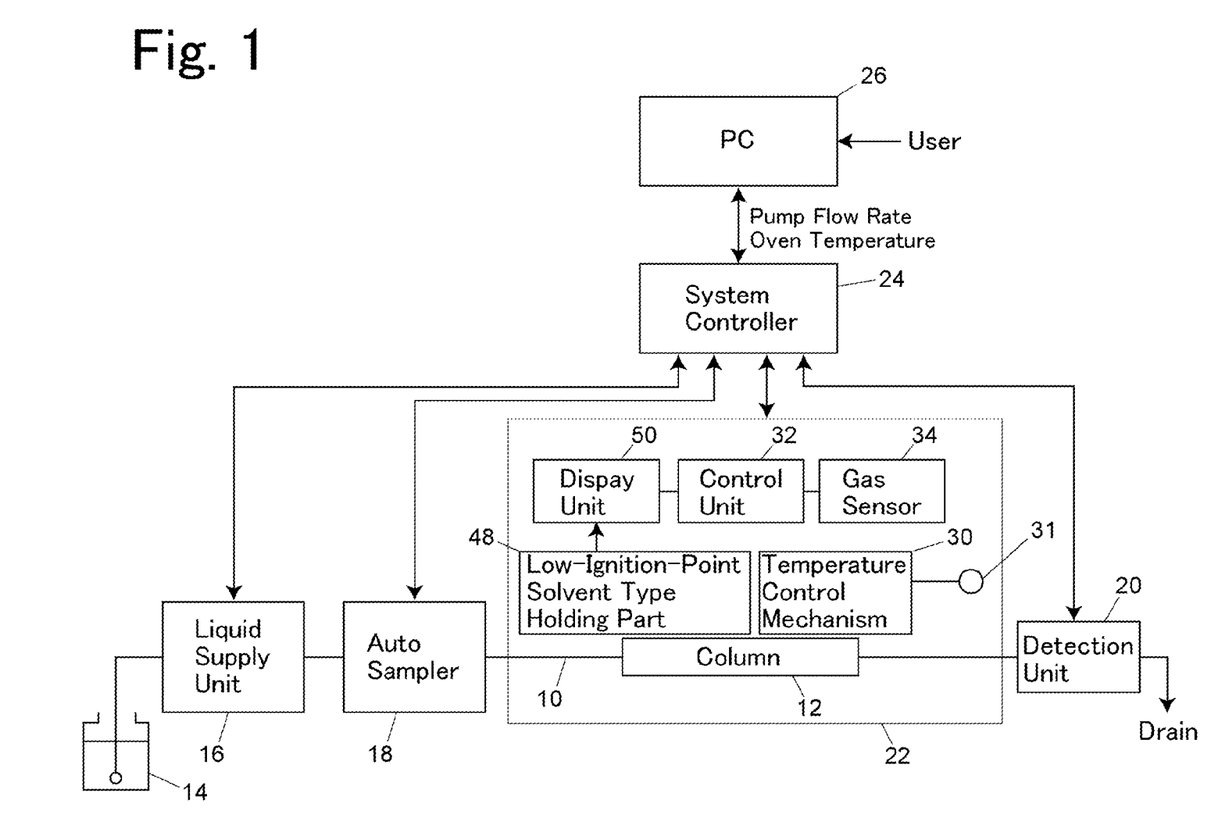
FIG. 1 is a block diagram illustrating a liquid chromatograph in an example.

FIG. 1 illustrates a liquid chromatograph in an example. In order to supply a mobile phase 14 to an analysis flow path 10 including a separation column 12, a liquid supply unit 16 is provided at the most upstream side. As an example of the liquid supply unit 16, a liquid supply unit including a liquid supply pump and configured to have independent functions is used. The liquid supply unit 16 is connected to a system controller 24, and mobile-phase supplying operations are controlled according to conditions set in the system controller 24.

In order to inject a sample into the analysis flow path 10 which is supplied with the mobile phase 14, a sample injecting unit 18 is provided in the analysis flow path 10 between the liquid supply unit 16 and the separation column 12. An auto sampler 18 is used as an example of the sample injecting unit 18. The auto sampler 18 is also connected to the system controller 24 and injects a sample set in the system controller 24 in a set amount into the analysis flow path 10.

A detection unit 20 that detects a sample ingredient eluted from the separation column 12 is provided in the analysis flow path 10 located downstream from the separation column 12. The detection unit 20 includes a flow cell in which the eluate from the separation column 12 flows, and includes a light detector that irradiates the flow cell with excitation light to detect generated fluorescence. The light detector of the detection unit 20 is also connected to the system controller 24, and a detection signal from the light detector is incorporated into the system controller 24, so that data processing is performed.

The separation column 12 is housed within a column oven 22, and the column oven 22 includes a temperature control mechanism 30 for maintaining the separation column 12 at a constant temperature. The temperature control mechanism 30 is an air-circulation system temperature control mechanism which includes a block heater as a heat source, and a circulation mechanism that circulates air within the column oven 22. The temperature control mechanism includes a temperature sensor 31 and maintains the inside of the column oven 22 at a constant temperature by feedback control that controls the electricity supplied to the block heater so that the inside of the column oven has a constant temperature. A control unit 32 is provided in order to control the temperature control mechanism 30.

In the present example, the control unit 32 also functions as a control unit for detecting a liquid leakage from the analysis flow path 10 within the column oven 22. However, the present invention is not limited thereto, and the control unit of the temperature control mechanism 30 and the control unit for detecting a liquid leakage can also be realized as separate control units. The control unit 32 is a computer, such as a microprocessor, which is provided in the column oven 22 in the present example. However, the control unit 32 can also be provided within the system controller 24, and in this case the control unit 32 is realized as a function of the system controller 24. Further, the control unit 32 can also be realized by a personal computer (PC) 26 as a general-purpose computer which is connected to the outside.

The system controller 24 is connected to the personal computer 26. Software for controlling each unit connected to the system controller 24, namely the liquid supply unit 16, the auto sampler 18, the column oven 22 and the detection unit 20, is installed in the personal computer 26. The personal computer 26 issues, to the system controller 24, an instruction such as a mobile phase to be supplied by the liquid supply unit 16 and an amount of the mobile phase to be supplied, a sample to be injected from the auto sample 18 and an amount of the sample to be injected, an oven temperature in the column oven 22, and a wavelength of fluorescence to be detected by the detection unit. The system controller 24 sends necessary analysis conditions to each unit to control operations of each unit, and further incorporates a detection signal from the detection unit 20 to perform data processing. The system controller 24 transmits, to the personal computer 26, results of the data processing based on a fluorescence signal of an eluted ingredient detected by the detection unit 20.

A display unit 50 such as a liquid crystal display device is provided so as to perform display for informing a user of a liquid leakage when the control unit 32 detects a liquid leakage, and other display. The display unit 50 may be a dedicated display unit for the column oven 22 or may be a display device of the personal computer 26.

Figure 2:
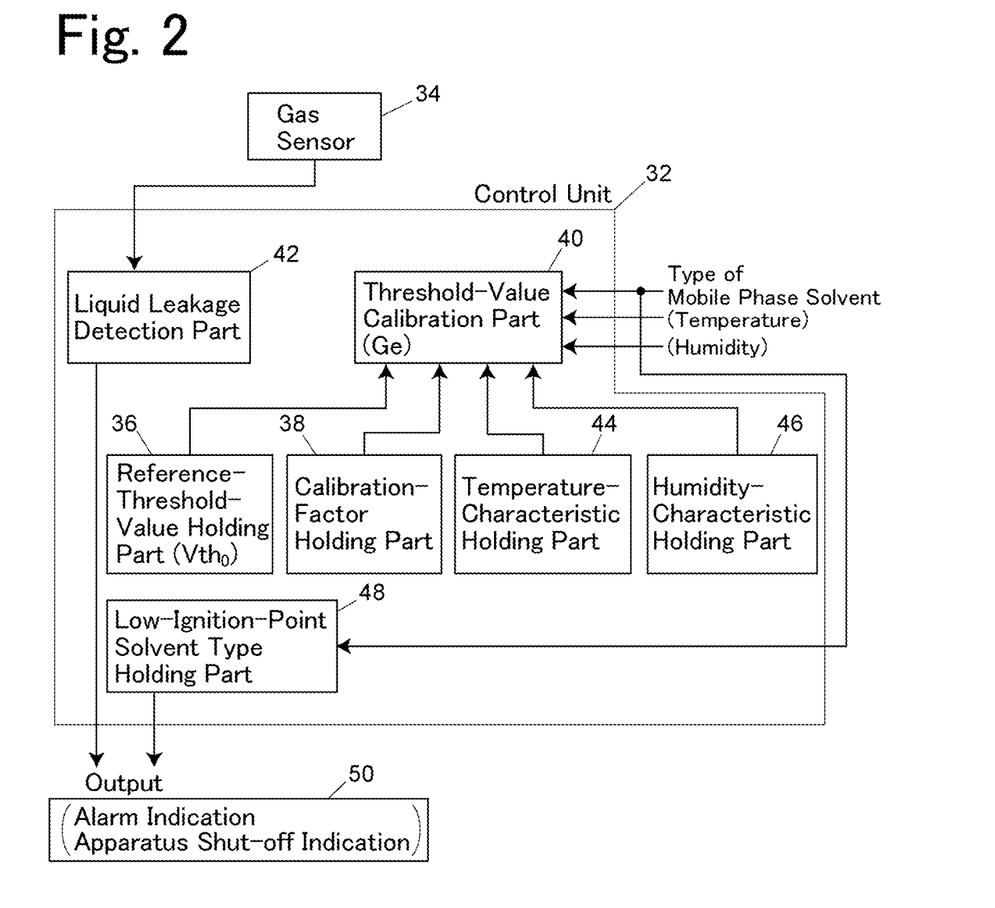
FIG. 2 is a block diagram illustrating a column oven in an example.

Within the column oven 22, a gas sensor 34 that detects a vaporized gas when the mobile phase leaks from the analysis flow path 10 and the vaporized gas is generated from the solvent forming the mobile phase, is provided. The control unit 32 controls the operations of the temperature control mechanism 30, and also functions as a control unit that incorporates detection output from the gas sensor 34 and compares the detection output with a threshold value to determine whether or not there is a liquid leakage from the analysis flow path 10. A configuration of the control unit 32 for determining such a liquid leakage is illustrated in FIG. 2.

In order to determine a liquid leakage, the control unit 32 includes a reference-threshold-value holding part 36 that holds, as a reference threshold value $V_{tho}$, a threshold value determined from a detected value resulted from measurement by the gas sensor 34 for a vaporized gas of a certain solvent, a calibration-factor holding part 38 that preliminarily holds, as a device constant, a calibration factor Ge indicating a difference between sensitivities of the gas sensor 34 to different solvents, a threshold-value calibration part 40 that calculates a threshold value $V_{th}$ from the reference threshold value $V_{tho}$ held in the reference-threshold-value holding part 36 and from the calibration factor Ge held in the calibration-factor holding part 38, according to $$V_{th}=V_{tho}\times Ge,$$

when a type of the solvent to be used is input, and a liquid leakage detection part 42 that compares a detected value from the gas sensor 34 with the threshold value calculated by the threshold-value calibration part 40 to detect a liquid leakage within the column oven 22, during use of the column oven.

In a further preferable example, the control unit 32 further includes a temperature-characteristic holding part 44 that holds a temperature characteristic of the sensitivity of the gas sensor 34. In this case, the threshold-value calibration part 40 is configured to calculate the threshold value $V_{th}$, further based on the temperature characteristic held in the temperature-characteristic holding part 44.

In a further preferable example, the control unit 32 further includes a humidity-characteristic holding part 46 that holds a humidity characteristic of the sensitivity of the gas sensor 34. In this case, the threshold-value calibration part 40 is configured to calculate the threshold value $V_{th}$, further based on the humidity characteristic held in the humidity-characteristic holding part 46.

In a further preferable example, the control unit 32 includes a low-ignition-point solvent type holding part 48 that holds a type of a solvent having a lower ignition point. The control unit 32 is configured to cause the display unit 50 to provide display for urging a user to be careful, when the type of the solvent to be used is input and when the input type of the solvent to be used agrees with the type of solvent held in the low-ignition-point solvent type holding part 48.

The reference-threshold-value holding part 36, the calibration-factor holding part 38, the temperature-characteristic holding part 44 and the low-ignition-point solvent type holding part 48 are realized by a storage device such as a nonvolatile semiconductor memory device such as a PROM, EPROM and EEPROM in the computer constituting the control unit 32, or a disk device. The threshold-value calibration part 40 and the liquid leakage detection part 42 are realized by software installed in the computer constituting the control unit 32, as functions of this computer.

Specifically, in the reference-threshold value holding part 36 of the control unit 32, a detected value from the gas sensor 34 for a certain solvent such as methanol obtained when the solvent has a concentration corresponding to, for example, ¹⁄₂₀ of the explosive limit concentration of a vaporized gas of the solvent is set as a threshold value. The detected value from the gas sensor 34 also has dependency on the temperature and the humidity as well as on the concentration of the solvent gas, and therefore, a reference threshold value at a certain temperature and humidity, such as a temperature of 20° C. and relative humidity of 65% is set as the reference threshold value.

The calibration-factor holding part 38 holds the calibration factor Ge set as a device constant. Since a sensitivity characteristic of the gas sensor is preliminarily known from literature and the like, the calibration factor Ge can be determined from a known literature value. Furthermore, the calibration factor Ge can also be determined from an actual measurement value resulting from measurement performed at a predetermined solvent concentration. The calibration factor Ge is not a factor measured for each gas sensor of an individual column oven, but is a factor preliminarily set as a device constant.

Data in the temperature-characteristic holding part 44 and the humidity-characteristic holding part 46 is also available as literature data. Furthermore, the data can be set using data resulting from actual measurement.

When the liquid leakage detection part 42 detects a liquid leakage, as output thereof, for example, the display unit 50 can be caused to display the fact that there is a the liquid leakage, the supply of the mobile phase can be stopped in order to stop the operation of the liquid chromatograph, or the operation of the column oven can be stopped.

Figure 3:
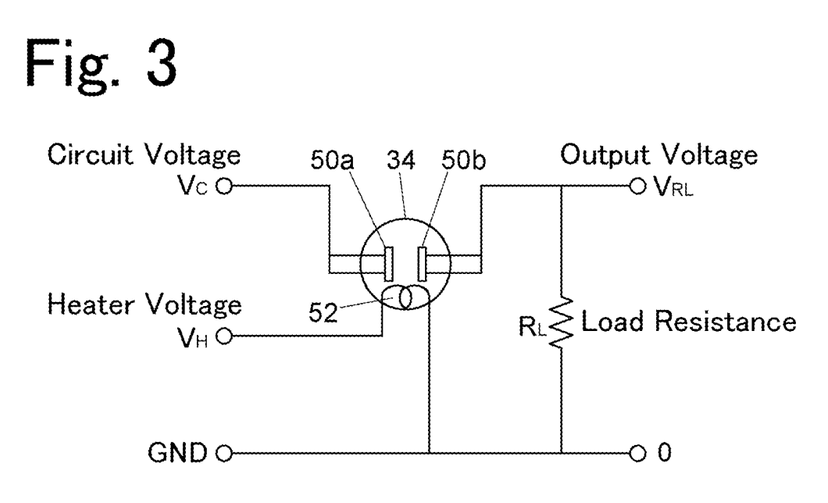
FIG. 3 is a circuit illustrating an example of a gas sensor.

FIG. 3 illustrates an example of the gas sensor. The gas sensor 34 is not particularly limited and, for example, the gas sensor 34 uses a tin oxide ($SnO_2$) semiconductor layer with low electric conductivity, as a functional layer on which a gas adsorbs. The gas sensor 34 includes a pair of electrodes 50a and 50b which are opposed to each other on the functional layer on which a vaporized gas of a solvent adsorbs, and a heater 52 that maintains the functional layer at a constant temperature. A constant voltage $V_H$ is applied to the heater 52, so that the functional layer is maintained at a constant temperature. When a circuit voltage $V_C$ is applied to one electrode 50a and the other electrode is grounded through a load resistance $R_L$, a voltage resulting from dividing the circuit voltage $V_C$ by the resistance $R_S$ between the electrodes 50a and 50b and the load resistance $R_L$ is output as an output voltage $V_{RL}$. The vaporized gas of the solvent adsorbs on the functional layer between the electrodes 50a and 50b, whereby the resistance $R_S$ between these electrodes decreases, and the output voltage $V_{RL}$ increases.

Figure 4:
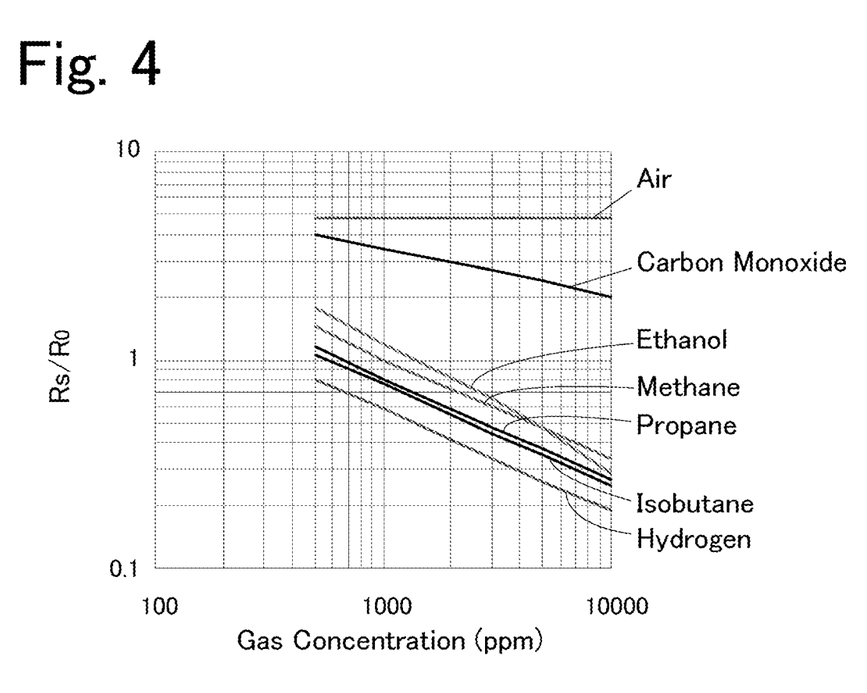
FIG. 4 is a graph illustrating a sensitivity characteristic of the gas sensor for each vaporized solvent gas.

The sensitivity characteristic which indicates the resistance value $R_S$ between the electrodes 50a and 50b differs depending on the type of the solvent gas. FIG. 4 illustrates a representative sensitivity characteristic of the gas sensor (refer to Non-Patent Document 1), and illustrates a situation where the resistance value $R_S$ changes depending on the type of a gas that adsorbs in the gas sensor. The lateral axis represents the gas concentration, while the longitudinal axis represents the ratio of the resistance value $R_S$ of methane and other gasses to a resistance value $R_O$ of a reference gas, where $R_O$ is the resistance value of the reference gas (in this case, methane) having a concentration of 1000 ppm. Here, acrylonitrile and the like, which are frequently used in a liquid chromatograph, are not described, but also indicate a similar sensitivity characteristic of decrease in the resistance value with increase in the concentration.

Figure 5:
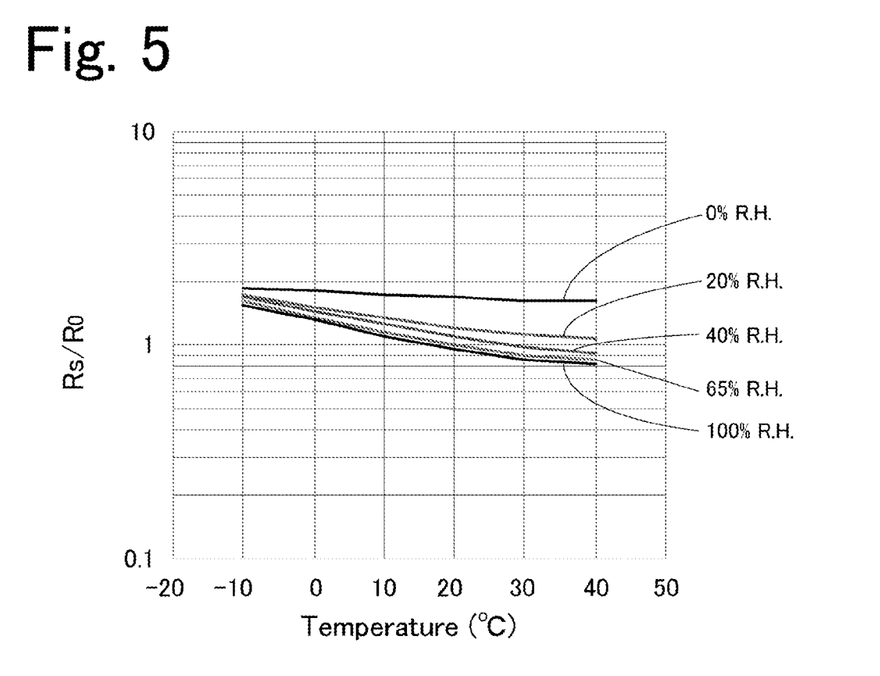
FIG. 5 is a graph illustrating temperature/humidity dependency of the gas sensor.

The sensitivity characteristic of the gas sensor also has dependency on the temperature and the humidity as illustrated in FIG. 5. FIG. 5 illustrates a representative sensitivity characteristic of the gas sensor which indicates dependency on the temperature and the humidity (refer to Non-Patent Document 1), and the lateral axis represents the temperature, while the longitudinal axis represents the ratio of the resistance value $R_S$ of methane and other gasses to $R_O$, where $R_O$ is the resistance value at a temperature of 20° C. and relative humidity (room humidity) of 65% RH of the reference gas (in this case, methane) having a concentration of 1000 ppm.

The sensitivity characteristic, the temperature dependency and the humidity dependency of the gas sensor, which are indicated by the resistance value $R_S$, vary among respective different gas sensors. However, when the sensitivity characteristic, the temperature dependency, and the humidity dependency are indicated as a relative value ($R_S/R_O$) of the resistance of the vaporized gas with respect to the resistance of the certain gas, as illustrated in FIGS. 4 and 5, they do not vary among respective different gas sensors. The sensitivity characteristic, the temperature dependency, and the humidity dependency which are indicated as the relative value ($R_S/R_O$) as illustrated in FIGS. 4 and 5 are available as literature values. Furthermore, the relative value preliminarily determined by performing measurement on a certain sensor can also be applied to other gas sensors of the same type.

The calibration factor Ge held in the calibration factor holding part 38 is a ($R_S/R_O$) value for each solvent when ($R_S/R_O$) of a certain solvent at a concentration corresponding to a threshold value for the certain solvent, for example, 1000 ppm, is assumed to be 1 based on the above-described literature value, or based on the sensitivity characteristic as in FIG. 4 obtained through measurement. When the type of the solvent is input, the threshold-value calibration part 40 selects and extracts a calibration factor corresponding to this solvent from among calibration factors Ge held in the calibration-factor holding part 38.

The temperature-characteristic holding part 44 and the humidity-characteristic holding part 46 hold data of a graph as illustrated in FIG. 5. Such data is also available as a literature value and is data determined by performing measurement on a certain gas sensor. When the threshold value is corrected, taking the temperature and the humidity into account, the calibration factor holding part 38 holds the calibration factor Ge for each solvent, together with a reference temperature and humidity. Therefore, when a temperature and humidity are input, the threshold-value calibration part 40 corrects the calibration factor, using ($R_S/R_O$) corresponding to the input temperature and humidity, assuming that ($R_S/R_O$) at the reference temperature and humidity is 1. The same applies when only either the temperature or the humidity is taken into account.

Figure 6:
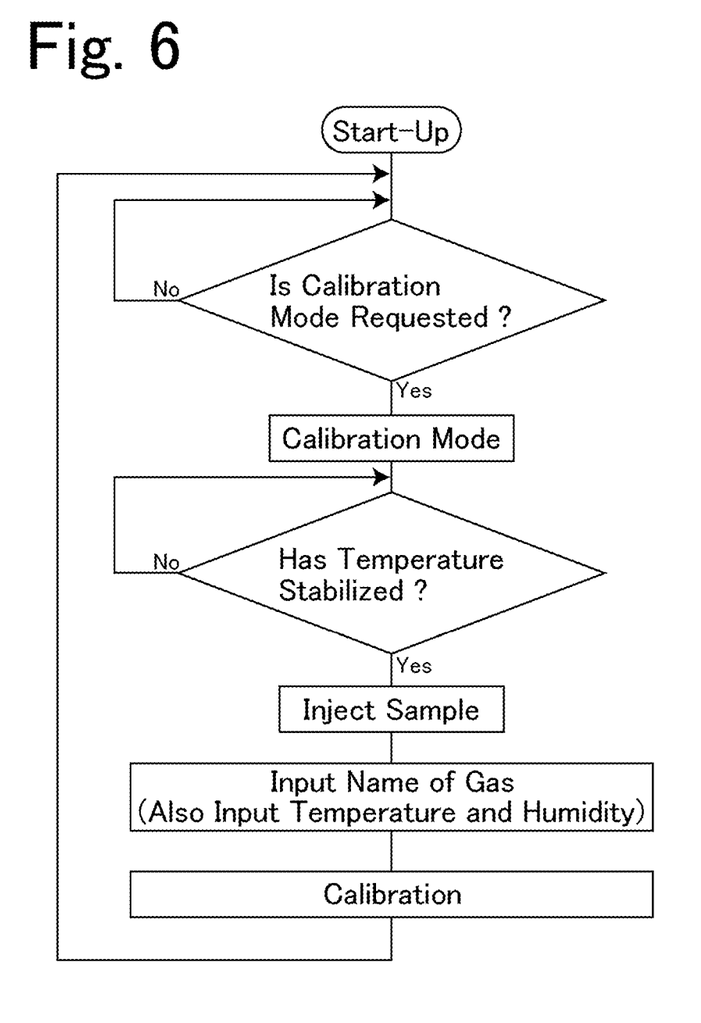
FIG. 6 is a flow chart illustrating operations at the time of calibrating the gas sensor in an example.

FIG. 6 illustrates operations when the reference threshold value for the certain solvent is set in the reference-threshold-value holding part 36 at the time of shipping the column oven from a factory.

The user inputs the fact of calibrating the gas sensor 34, through the system controller 24 or by directly manipulating the column oven 22. The type of the certain solvent to be calibrated, and the calibration reference temperature of the column oven 22 are input. For example, an instruction indicating that the type of the certain solvent is methanol and the calibration reference temperature of the column oven 22 is 50° C. is assumed to be issued.

The control unit 32 shifts to a calibration mode, on receiving the instruction from the system controller 24 or on receiving the instruction issued through direct input to the column oven 22. In the calibration mode, the control unit 32 performs temperature control by using the temperature control mechanism 30 and the temperature sensor 31, so that the temperature within the column oven 22 reaches the calibration reference temperature. When the temperature in the column oven 22 is stabilized at the calibration reference temperature, the control unit 32 urges the user to inject a sample so that the gas concentration within the oven reaches the calibration reference concentration, by using the display unit 50.

The user injects a predetermined amount of the certain solvent, so that the concentration within the column oven 22 reaches the calibration reference concentration. Since the volumetric capacity of the inside of the column oven 22 is known, the amount of the solvent to be injected can be determined from the calibration reference concentration within the column oven 22. The calibration reference concentration is a concentration to serve as the threshold value. However, even when the certain solvent is injected so that another concentration is reached, it is possible to determine the detected value from the gas sensor at the calibration reference concentration by calculations from the relationship between the sensitivity characteristic and the concentration in FIG. 4.

It is confirmed that the concentration within the column oven 22 has reached the calibration reference concentration, and the detected value $V_{RL}$ from the gas sensor 34 at that time is stored as the reference threshold value $V_{tho}$ in the reference-threshold-value holding part 36. It is possible to determine that the calibration reference concentration has been reached, by the fact that the output from the gas sensor 34 has been stabilized. The calibration reference temperature and the humidity at that time are also stored in the reference-threshold-value holding part 36, together with the reference threshold value $V_{tho}$. The room humidity is input as the humidity.

Figure 7:
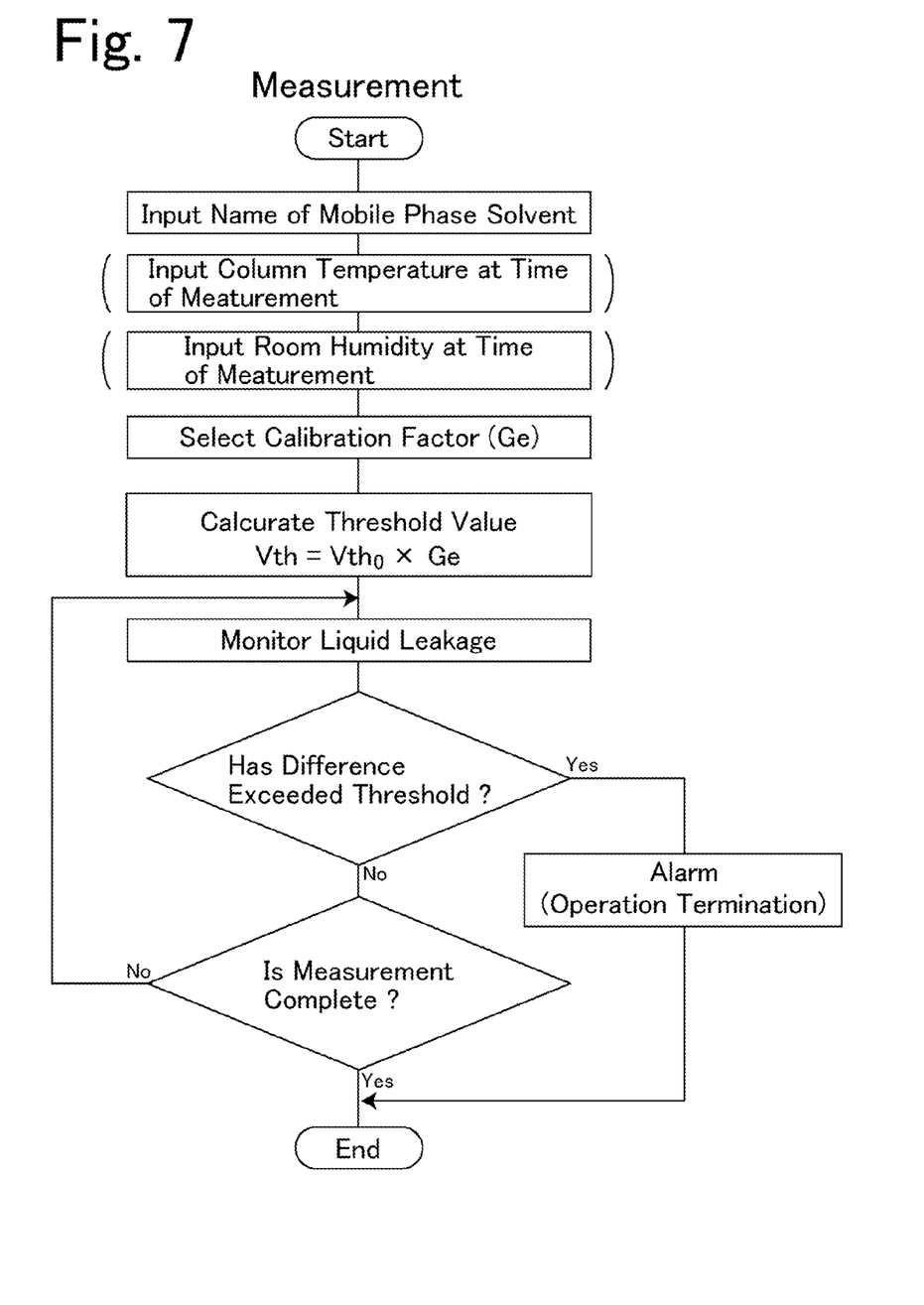
FIG. 7 is a flow chart illustrating operations of the column oven in an example.

FIG. 7 illustrates operations when measurement is performed in a state where the reference threshold value $V_{tho}$ is held as described above.

Figure 8:
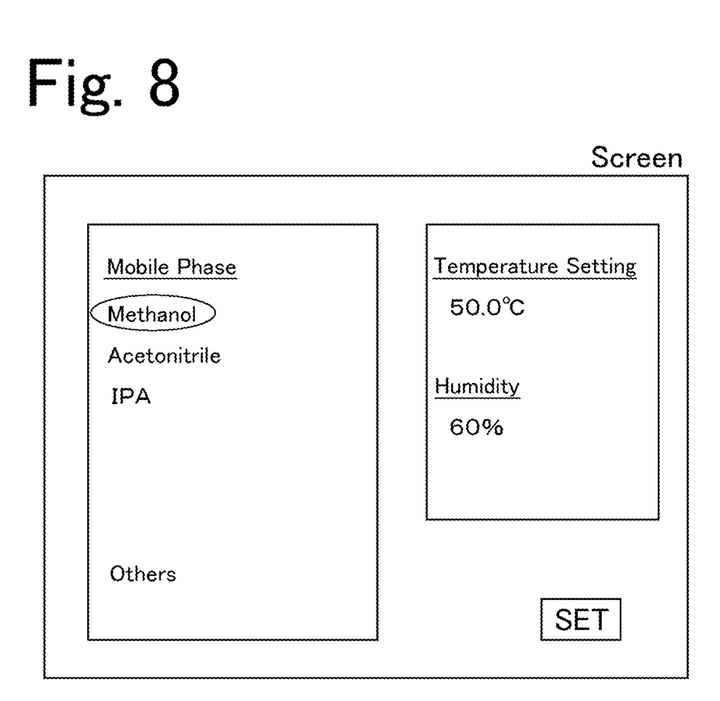
FIG. 8 is a view illustrating a display screen for inputting conditions to the column oven in the same example.

In starting a measurement operation, the user inputs the type of the solvent forming the mobile phase to be used, to the system controller 24 or the column oven 22. The user performs the input while viewing the screen of the display unit 50 as illustrated in FIG. 8, for example. Here, a case is illustrated where methanol is input as the solvent in the mobile phase. Further, when where the threshold value is also corrected according to the temperature and the humidity, a set temperature of the column oven and humidity are also input. As the set temperature of the column oven, the control unit 32 may automatically incorporate a temperature detected by the temperature sensor 31 within the column oven 22, besides the mode of inputting as described above. As the humidity, the room humidity is input.

When the mobile phase includes a single solvent, the type of this solvent is input as the solvent in the mobile phase. When the mobile phase is a mixture of two or more solvents, the type of the solvent that allows a low threshold value to be set, namely the type of the solvent having a lower explosive limit concentration is input. The same applies to a case where the composition of the mobile phase changes with time in gradient analysis. When one solvent of the mixture is water, water is not regarded as a solvent serving for setting the threshold value.

When the type of the solvent is input, the threshold-value calibration part 40 of the control unit 32 calls the reference threshold value $V_{tho}$ out of the reference-threshold-value holding part 36 and calls the calibration factor Ge for the input solvent out of the calibration-factor holding part 38 to calculate the threshold value $V_{th}$ for the input solvent according to Equation (1). In a mode where one or both the temperature and the humidity are taken into account, the threshold-value calibration part 40 corrects the threshold value $V_{th}$ based on the data held in the temperature-characteristic holding part 44 and the humidity-characteristic holding part 46.

Thus, an environment which enables use of the column oven 22 is arranged. When an operation of the liquid chromatograph including the column oven 22 is started, the liquid-leakage detection part 42 monitors a liquid leakage, while comparing the detection output from the gas sensor 34 with the threshold value $V_{th}$ in the threshold-value calibration part 40.

When the detection output from the gas sensor 34 exceeds the threshold value $V_{th}$ during monitoring, the display unit 50 is caused to display an alarm, the operation of the liquid chromatograph is stopped, or other operations are performed.

DESCRIPTION OF REFERENCE SIGNS

10: Analysis flow path
12: Separation column
14: Mobile phase
16: Liquid supply unit
18: Auto sampler
20: Detection unit
22: Column oven
34: Gas sensor
36: Reference-threshold-value holding part
38: Calibration-factor holding part
40: Threshold-value calibration part
42: Liquid-leakage detection part
44: Temperature-characteristic holding part
46: Humidity-characteristic holding part
48: Low-ignition-point solvent type holding part
50: Display unit

What is claimed is:

1. A column oven for performing temperature control on a separation column in a liquid chromatograph, comprising:
a gas sensor for detecting a vaporized gas of a solvent forming a mobile phase;
a reference-threshold-value holding part for holding, as a reference threshold value $V_{tho}$, a threshold value determined from a detected value resulting from measurement by the gas sensor, for a vaporized gas of a certain solvent having a lower concentration than an explosive limit concentration;
a calibration-factor holding part for preliminarily holding, as a device constant, a calibration factor Ge indicating a difference between sensitivities of the gas sensor to different solvents;
a threshold-value calibration part for calculating a threshold value $V_{th}$ from the reference threshold value $V_{tho}$ held in the reference-threshold-value holding part and from the calibration factor Ge held in the calibration-factor holding part, according to $$V_{th} = V_{tho} \times Ge,$$

when a type of a solvent to be used is input; and
a liquid leakage detection part for comparing a detected value from the gas sensor with the threshold value calculated by the threshold-value calibration part to detect a liquid leakage within the column oven, during use of the column oven.

2. The column oven according to claim 1, further comprising a temperature-characteristic holding part for holding a temperature characteristic of the sensitivity of the gas sensor, wherein the threshold-value calibration part calculates the threshold value $V_{th}$, further based on the temperature characteristic held in the temperature-characteristic holding part.

3. The column oven according to claim 1, further comprising a humidity-characteristic holding part for holding a humidity characteristic of the sensitivity of the gas sensor,
wherein the threshold-value calibration part calculates the threshold value $V_{th}$, further based on the humidity characteristic held in the humidity-characteristic holding part.

4. The column oven according to claim 1, further comprising a low-ignition-point solvent type holding part for holding a type of a solvent having a low ignition point,
wherein, when the type of the solvent to be used is input and when the input type of the solvent to be used agrees with the type of the solvent held in the low-ignition-point solvent type holding part, a display unit is caused to provide display for urging a user to be careful.

5. The column oven according to claim 1, wherein
the reference-threshold-value holding part holds reference threshold values in plural stages, as the reference threshold value $V_{tho}$, and
an alarm or another output form is differentiated depending on a liquid leakage detected based on a threshold value derived from among the reference threshold values in the plural stages.

6. A liquid chromatograph comprising:
a liquid supply unit for supplying a mobile phase to an analysis flow path including a separation column;
a sample injecting unit for injecting a sample into the analysis flow path between the liquid supply unit and the separation column; and
a detection unit for detecting a sample ingredient eluted from the separation column,
wherein the column oven according to claim 1 is used as a column oven for performing temperature control on the separation column.

* * * * *